United States Patent

Metsch et al.

[11] Patent Number: 5,935,097
[45] Date of Patent: Aug. 10, 1999

[54] SUCTION AND RINSING INSTRUMENT

[75] Inventors: Dieter Metsch, Kraichtal-Bahnbrücken; Manfred Boebel, Oethisheim; Gerhard Fritz Buess; Marc O. Schurr, both of Tübingen; Klaus Roth, Ofterdingen, all of Germany

[73] Assignee: Richard Wolf GmbH, Knittlingen, Germany

[21] Appl. No.: 08/879,942

[22] Filed: Jun. 20, 1997

[30] Foreign Application Priority Data

Jun. 21, 1996 [DE]  Germany .......................... 196 24 811

[51] Int. Cl.[6] ..................................................... A61M 1/00
[52] U.S. Cl. ................... 604/27; 604/43; 604/19; 604/21; 604/118; 600/127; 600/156; 607/115; 606/39; 606/46; 606/49; 606/37
[58] Field of Search ................... 604/43, 33, 34, 604/35, 902, 39, 27, 19, 21, 30, 118, 173; 600/127, 128, 130, 129, 156, 157; 607/115; 606/39, 45, 47, 49, 37, 46

[56] References Cited

U.S. PATENT DOCUMENTS

| 5,230,704 | 7/1993 | Moberg et al. . |
| 5,273,524 | 12/1993 | Fox et al. . |
| 5,514,089 | 5/1996 | Walbrink et al. . |

FOREIGN PATENT DOCUMENTS

| 0 546 767 A2 | 6/1993 | European Pat. Off. . |
| 0 638 279 A1 | 2/1995 | European Pat. Off. . |
| 41 19 592 A1 | 12/1992 | Germany . |
| 92 10 590 | 2/1993 | Germany . |
| 41 31 495 C1 | 4/1993 | Germany . |
| 296 02 736 U1 | 5/1996 | Germany . |

*Primary Examiner*—Wynn Wood Coggins
*Assistant Examiner*—N. Kent Gring
*Attorney, Agent, or Firm*—Panitch Schwarze Jacobs & Nadel, P.C.

[57] ABSTRACT

The invention relates to a suction/rinsing instrument comprising a suction channel for removing fluid and a rinsing channel for supplying rinsing fluid. The suction channel is provided for receiving an auxiliary instrument. Via a grip part of the instrument, the auxiliary instrument, for example a forceps, may be controlled. The auxiliary instrument is fixed on the suction/rinsing instrument by way of a receiver. The receiver can be traversed in the axial direction of the shank, the traversing is effected via operating means provided on or near the grip part, so that the operator, without having to let go of the grip part, may selectively, with only one hand, push forward the auxiliary instrument an thus operate or also retract the auxiliary instrument and clear the suction/rinsing channel.

13 Claims, 6 Drawing Sheets

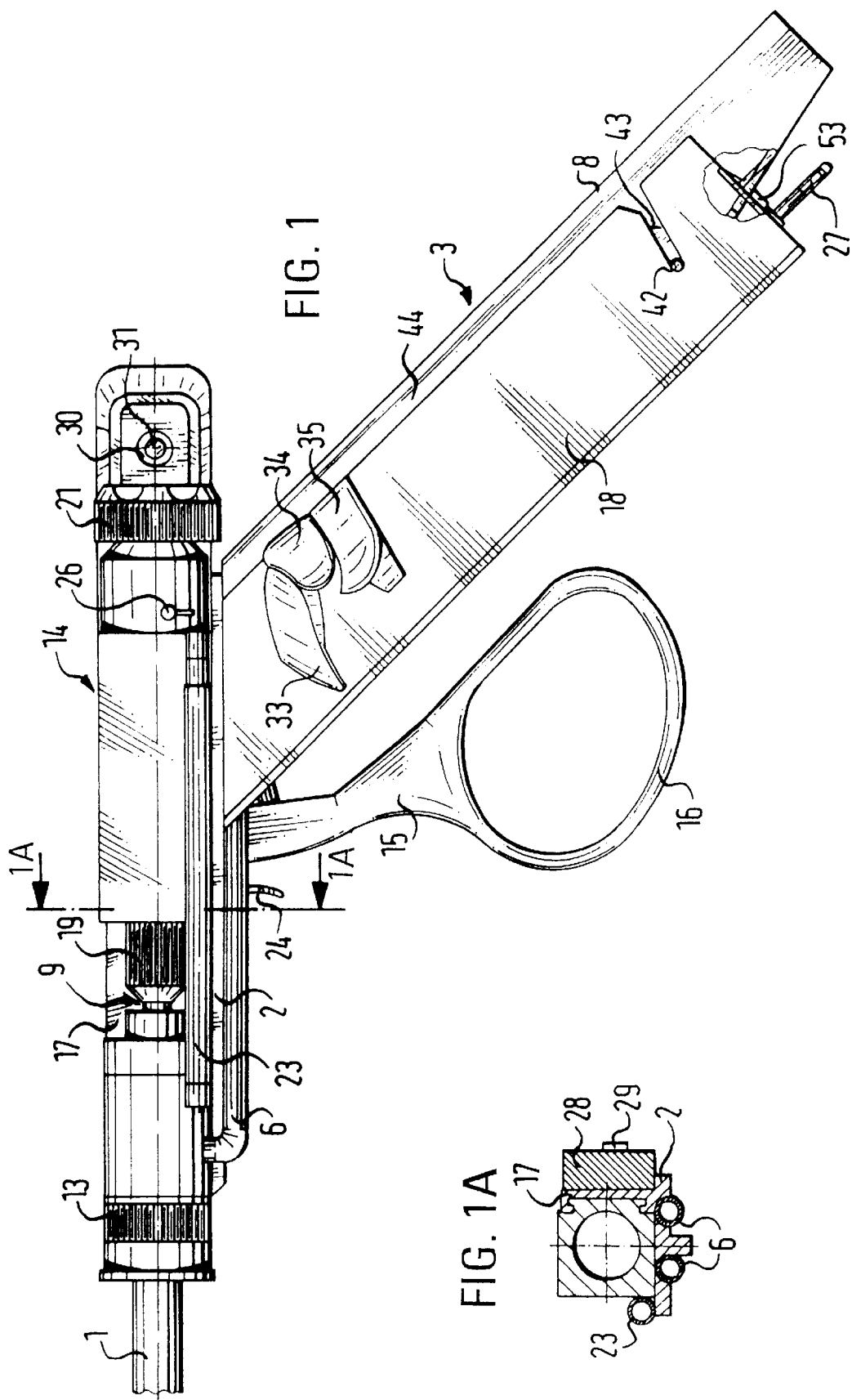

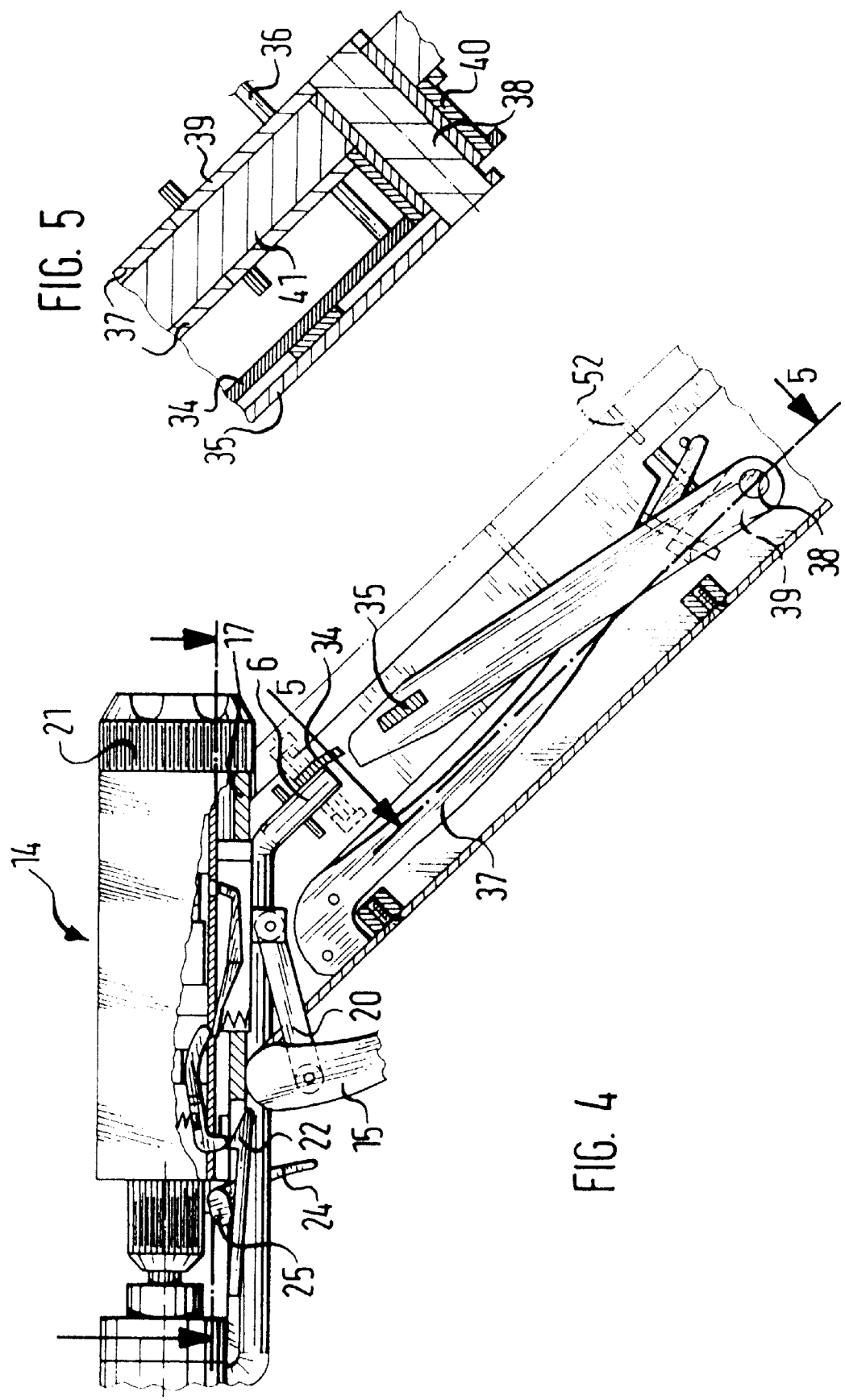

SUCTION AND RINSING INSTRUMENT

BACKGROUND OF THE INVENTION

The invention relates to a suction and rinsing instrument according the features specified in the earlier part of claim 1.

Suction and rinsing instruments of this type are employed with endoscopic operations in order to maintain a clear view of the operational area, observable with the endoscope optic within the body cavity, by way of rinsing as well as subsequent aspiration of rinsing fluid, body fluid, tissue particles and likewise, and to carry off tissue removed during the operation or other parts out of the body cavity. Whilst the channel for supplying the rinsing fluid may have a relatively small cross section, the suction channel leading back must have a considerably larger free lumen, in order for example to let through tissue parts, coagulate, blood and likewise. On the other hand, with endoscopic instruments of this type one is constantly striving the keep the outer diameter of the instrument as small as possible, in order to traumatize the patient as little as possible.

Usually suction/rinsing instruments of the previously described type are applied in combination with a further auxiliary instrument, for example forceps, scissors, a probe or likewise. Such an instrument is for example known from DE-A-41 19 592. Due to the minimalized dimensions of the outer circumference is the case that the suction-rinsing procedure may only be effected when the auxiliary instrument is pulled so far back that the distal channel end section is cleared. On the other hand, the auxiliary instrument may only be employed when its tool protrudes beyond the shank on the distal side. Finally it is desirable to combine as many functions in one instrument as possible and where possible to be able to control these with only one hand.

From EP-A-0 546 767 there is known a suction/rinsing instrument into which an auxiliary instrument, for example a forceps or scissors may be inserted, and which is designed on the grip side such that with the hand located on the grip part, the suction-rinsing function as well as the operation of the forceps may be controlled. For this, the instrument is fastened in a receiver and it may be exchanged or removed during the endoscopic operation without having to pull the instrument shank from the body cavity, in particular from the trocar sleeve. The instrument is sealed via a valve so that also when the auxiliary instrument is removed, the pressurized gas brought into the body cavity may not escape. Although this instrument is suitable, with the instrument once inserted, for a one-handed operation, it is usual however for rinsing and aspirating to remove the instrument or at least to retract it so far back that the rinsing and suction channel is cleared. This may only be accomplished with the help of a second hand. Moreover, it is often particularly necessary when working with scissors or a coagulation instrument to activate the rinsing and suction procedure. In this regard, the application of this instrument in combination for example with an auxiliary instrument in the form of a forceps invisages considerable handling problems. Although, in combination with an HF electrode, there is shown an auxiliary instrument with which it can be simultaneously rinsed and suctioned, this however may only be effected with a very special and thin wire electrode, since otherwise the free space for the suction channel is too small. Furthermore, the electrode inhibits the aspiration procedure since the suction tube end may not be guided closely enough to the suction location.

BRIEF SUMMARY OF THE INVENTION

Proceeding from this, it is the object of the invention to provide a suction/rinsing instrument which can be operated with one hand and with which alternately, the suction and rinsing procedure may be effected without problems but on the other hand the operation of an auxiliary instrument is possible without having to enlarge the instrument diameter.

According to the invention this object is achieved by those feature specified in the latter part of claim 1.

The invention thus provides for the receiver, within which the auxiliary instrument is fastened, to be traversable in the axial direction of the shank and to so arrange corresponding operating means for traversing this receiver on the grip part or near the grip part, that it may be operated with the hand located on the grip part. In this manner, it is possible for the operating surgeon, without having to let go of his hand from the grip part of the suction and rinsing instrument, to retract the auxiliary instrument for the purpose of suctioning and rinsing or to traverse the auxiliary instrument forwards for the purpose of treatment with the auxiliary instrument. As such, the auxiliary instrument remains fixed and locked in the instrument receiver so that in this way the reliable seating of the auxiliary instrument and the operating possiblility is not inhibited.

Particularly with scissors and forceps, the orientation of the pivoting axis or the jaw parts to the instrument axis is important. The invention thus provides, in an advantageous further development, for the auxiliary instrument to be rotatably arranged within the receiver, and operting means to be provided near to the grip part, so that also a turning of the auxiliary instrument without the need for a further hand is possible. Preferably here, a latchable turning in a stepped manner is provided so that the instrument locks in the respective adjusted positional orientation.

With regard to design, it is advantageous to let the shank be connected to a shank carrier arranged roughly on the same axis and to guide the receiver for the auxiliary instrument on this shank carrier in a carriage manner, as well to fasten the grip part in the shape of a hand grip. This shank carrier then forms the base carrying body of the whole instrument about which the instrument is more or less constructed. Such an arrangement is then particulary well suited when the instrument, as is already regularly required for medical instruments on hygenic grounds, is to be able to be dismantled. This arangement is also advantageous with regard to center of gravity in the region of the hand grip and the handling.

It is useful to releasably arrange the shank on the shank carrier, for example fixed to the shank carrier by way of a knurled nut. This simplifies the cleaning of the shank as well as the shank carrier and the channel running therein, and permits the use of the instrument with different shanks.

The suction and rinsing channels run into the distal part of the shank carrier from their outlet locations in the shank in channels which are provided within the shank carrier and which to a large extent are formed by tubes. The proximal end of these channels is formed by tube ends which although they lie within the shank carrier, however face in the direction of the grip part where they can be connected to hoses via a connecting cassette which is exchangeably fastened in the grip part. The channels are thus already guided in the region of the grip part via elastic hoses, the blocking or opening control of the suction and rinsing channels thus do not require to be effected via complicated and difficult to clean valves, but may be effected within the grip part via hose squeezing levers. Such hose squeezing levers are known for example from DE-U-92 10 590 or U.S. Pat. No. 5,230,704 and in this context are expressly referred to. The connecting cassette, which without any tool may be fixed within the grip part, accomodates the connecting hoses and fixes these within the instrument. On insertion of the connecting cassette, the connecting hoses are automatically pushed onto the free ends of the tubes in the shank carrier. The strain relief for the tubes is provided within the connecting cassette so that the tube-hose connection is constantly free of loading. Moreover the hoses may be removed quickly and simply from the connecting cassette when required and replaced with new ones. The corresponding control levers which block or open the hoses in the region of the connecting cassette by way of squeezing are provided in the grip part outside of the connecting cassette.

The instrument shank is preferably designed as is known from DE-A-41 19 592. Then, the distal shank end may be formed simultaneously as a coagulation and cutting electrode, which makes a tapering of the distal end section particularly useful. Moreover, such a reduced design of the distal end section is also already advantageous because in this way, the auxiliary instrument in this region is able to be guided considerably more precisely, which however has the disadvantage that the suction/rinsing channel in this region is almost completely closed by the auxiliary instrument.

In order to ensure that on the one hand it can be safely operated with the auxiliary instrument but on the other hand, the suction-rinsing procedure is not inhibited by the auxiliary instrument, this and the length carriage guide for the receiver are to be dimensioned such that in the forward end position of the receiver on the shank carrier, the tool part projects beyond the distal shank end and is operable from the grip part. In the retracted rearward end position of the receiver on the other hand, the tool must be completely inserted into the shank, this being so far that this distal end section is cleared and a sufficient free cross section arises, particularly for the suction channel.

The instrument according to the invention is also preferably designed as a combined suction/rinsing and coagulation instrument. As such the distal shank end is designed as an HF electrode and can be correspondingly supplied with current so that according to the supply of current, cutting as well as coagulation is possible. It is however particularly advantageous when the distal shank end iself or alternatively the auxiliary instrument itself are selectively subjectable to current, since then, also during the operation, coagulation may be effected with the auxiliary instrument. For this purpose the invention provides for an automatic change-over depending on the position of the receiver on the shank carrier. When the receiver is in the retracted rearward position in which the tool of the auxiliary instrument is completely inserted into the shank, the distal end of the shank can be supplied with current, and then, when the receiver on the shank carrier is arranged in the forward position, that is to say when the tool of the auxiliary instrument is completely extended, then the auxiliary instrument may be connected to a current source. This may be realized in a simple manner by a switch provided on the carriage.

Preferably the shank carrier comprises a retaining body with an approximate L-shaped cross section, in which the receiver is guided in a carriage manner. On the lower leg of this L-shaped retaining body, the grip part may then be fastened. From a design point of view, this is effected in a simple and stable manner by a U-shaped retaining body which connects here and which forms the carrying part of the grip part, onto which the required lever, bearing and rod assembly may be mounted and which is open towards the rear so that it may be formed on the rear side for receiving the connecting cassette.

On the other leg, directed upwards, of the L-shaped retaining body, externally, that is to say on the side distant to the receiver, there is fastened a housing part which comprises electrical and/or electronic components for controlling the current supply. In this housing part, which is accessible without any effort with the hand resting on the grip part, a change-over switch for the current supply type (cutting current or coagulation current) may for example be provided. Preferably, on this housing there is mounted a switch which controls the supply of current from the shank onto the auxiliary instrument or vice versa on traversing of the receiver. This switch may, since the L-profile itself is part of the carriage guide, by way of a recess in one leg, project into the carriage guide and at the same time be arranged on this housing part.

In order to prevent the suction or rinsing channel from opening by mistake on operation of the auxiliary instrument, there is provided a thumb rest on one side on the grip part, whilst nearby there lies the lever for controlling the supply and removal of fluid. A finger ring, arranged at the end of a lever, is mounted forward of the grip part, this finger ring serving the control of the auxiliary instrument, that is to say, for controlling a forceps or scissors. This lever is pivotably mounted in the shank carrier and engages from below into the recess via a further lever when the recess is in its forward end position, by which means a central push plunger rod of the auxiliary instrument is operated.

At a short distance forward of this lever with the finger ring there is mounted a further lever on the shank carrier which is likewise operable such that the hand need not be removed from the grip part. This release lever unlocks the receiver so that it is traversed to its rearward end position in which the auxiliary instrument is completely inserted into the shank. For traversing to the forward end position the receiver is pushed distally from the proximal end by thumb pressure until it latches in its forward end position. This operation is also effected without having to remove the hand from the grip part.

BRIEF DESCRIPTION OF THE DRAWINGS

The invention is hereinafter described in more detail by way of one embodiment example shown in the drawings. These show:

FIG. 1 a schematic representation of a lateral view of the proximal part of an instrument according to the invention, with the receiver in the forward position, FIG. 1A a cross-sectional view of the suction and rinsing instrument as shown in FIG. 1 taken along lines 1A—1A of FIG. 1, FIG. 2 a lateral view of the instrument from the side opposite to that in FIG. 1, FIG. 3 a lateral view of the instrument according to FIG. 1, but with the receiver in the rearward position, FIG. 4 the proximal part of the instrument in a representation similar to FIG. 1, but partly in section, FIG. 5 a section taken along line 5—5 in FIG. 4, FIG. 6 the connecting cassette removed from the grip part, this being in longitudinal section in FIG. 6a, a cross section taken along section line 6b—6b in FIG. 6b and in FIG. 6c, in a representation according to FIG. 6a, but in the opened position without hoses, FIG. 7 a longitudinal section through the receiver and FIG. 8 a further longitudinal section through the receiver in another section plane.

DETAILED DESCRIPTION OF THE INVENTION

Figure 3:
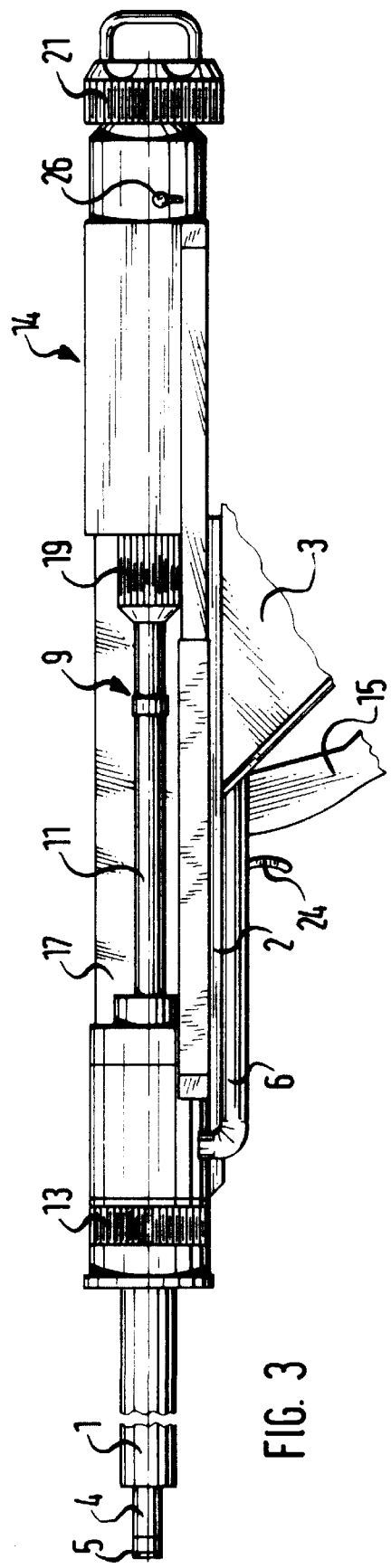
Figure 2:
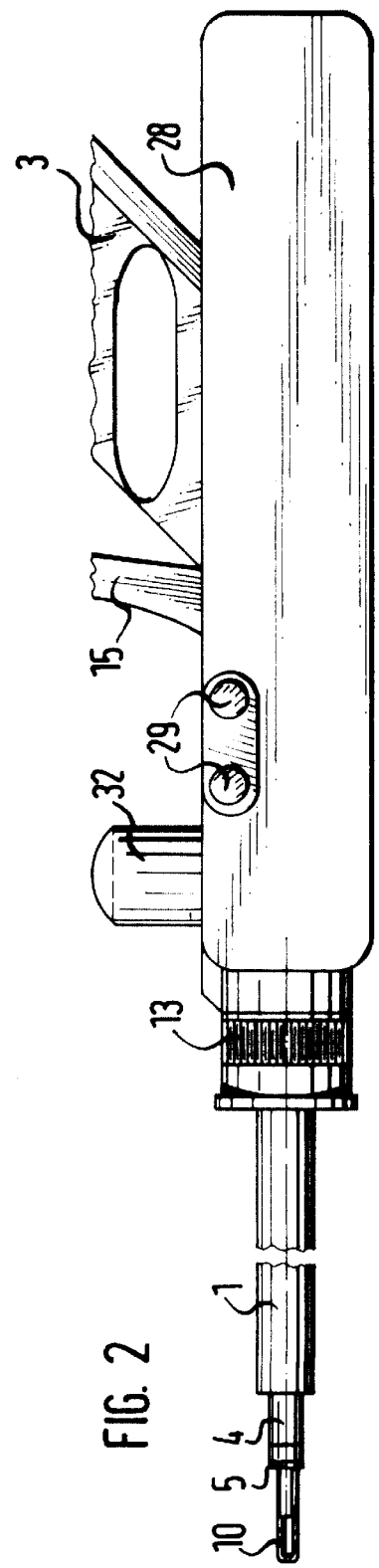

The instrument represented comprises a longitudinally extended shank 1 which connects releasably to a shank carrier 2 which elongates the shank proximally in the axial direction of the shank 1. Onto the shank carrier 2 there is mounted a hand grip 3 which is directed diagonally downwards and proximally, and which in the embodiment shown is envisaged for gripping with the right hand.

The shank 1 comprises a rinsing channel which is not shown and a suction channel, which extends over the whole length of the shank from the shank carrier 2 to a relieved distal end section 4 which has a smaller diameter than the remaining shank and into which these channels open. Such a shank is shown in DE-A-41 19 592, particularly by way of FIG. 9 to which it is referred to here. The distal shank end 5 is formed as a HF electrode and can be supplied with current in the known manner.

The shank 1 is releasably fastened to the shank carrier 2 by way of a knurled screw 13. Within the shank carrier 2, in the distal region where the shank 1 opens into the shank carrier 2, there are provided transverse channels (not shown) which connect the suction channel and the rinsing channel separately each to a tube 6 which is guided on the lower side of the shank carrier 2. These tubes 6 reach up to the hand grip 3 (see FIG. 4), where they are connected to elastic hoses 7 which are fixed and guided in a connecting cassette 8 which lies rigidly in the hand grip 3 in a releasable manner.

Within the shank 1, and more exactly within the comparatively large lumened central suction channel, there is an auxiliary instrument 9 arranged displaceable in the axial direction of the shank 1. With the auxiliary instrument 9 shown, it is the case of a forceps. The jaw part 10 arranged at the distal end is connected, in a manner known per se, to a tube 11 and a rod 12 guided therein, and in such a manner that the relative movement of the rod 12 in the axial direction of the tube 11 opens or closes the jaw part 10. The tube 11 of the auxiliary instrument 9 is guided with a slight amount of play within the end section 4, in the remaining region there results between this tube 11 and the shank 1 an annular suction channel which on one side is made narrower by the separately guided rinsing channel. The rod 12, in the distal region of the shank carrier, there where the shank 1 is fixed on the shank carrier, is guided through this in a sealed manner and is releasably fixed, by way of a knurled nut 19, in a receiver represented in detail by way of in FIGS. 7 and 8. The rod 12 reaches as far as into the receiver 14 where, via a lever mechanism, a coupling to a lever 15 with a finger ring 16, mounted in front of the hand grip 3, is effected in such a manner that on pivoting of the lever distally, the push rod 12 is also moved distally and vice versa.

The receiver 14 is formed roughly cuboid-shaped with a quadratic cross section and is displaceably guided on the shank carrier 2 in the axial direction of the shank 1 in a limited manner. For this, the shank carrier 2 comprises a cross section with an L-shaped profile 17 whose lower leg is connected to the retaining body 18 having a U-shaped cross section, of the hand grip 3, the free leg ends of which being directed proximally. The other leg of the L-profile lies roughly in the plane of the drawing in the representation according to FIG. 1. The auxiliary instrument 9 is fixed in the receiver 14 by way of a knurled nut 19. The receiver 14 comprises on its lower side a longitudinal recess in which an auxiliary carriage (not shown), guided in the lower leg of the L-profile 17 on an intermediate lever 20, is arranged. The intermediate lever 20 pulls this auxiliary carriage distally when the finger ring 16 is pivoted distally and vice versa. On the lower side of the receiver 14, the auxiliary carriage is connected to the rod 12 with a positive fit when the receiver is located in the forward end position shown in FIG. 1. In the rearward end position (shown in FIG. 3), the lever 15 is ineffective and is not movingly connected to the rod 12.

At the proximal end of the receiver 14 there is provided a knurled wheel 21 which is formed such that in the forward position of the receiver 14 shown in FIG. 1, it can be easily rotated with the thumb when the hand of the operator grips the hand grip 3. Within the receiver 14 there is provided a latching device which permits a stepwise turning of the whole auxiliary instrument 9 about the shank axis 1. In order to bring the receiver 14 from the rearward end position shown in FIG. 3 into the forward end position shown in FIG. 1, by bearing the thumb on the proximal end face of the knurled wheel 21, force in the distal direction is applied. During this, the hand grip 3 remains gripped by the hand. The receiver 14 then moves distally in its carriage guide upto its forward end position (FIG. 1) in which a spring cam 22, arranged in the lower side of the L-profile 17, engages into the receiver 14 and here fixes the receiver 14 in its end position via two spring loaded levers working in cooperation with one another and produces the mechanical connection to the lever 15. This movement of the receiver 14 distally is effected against a spring force of a compression spring arranged within the guiding tube so that after running past the spring cam 22, the receiver 14 is impinged by spring force in the proximal direction. The spring cam 22 engaging into the lower side of the receiver 14 at the same time forms, as can be recognized by way of FIG. 4, the mechanical connection of the lever 15 to the intermediate lever 20 and the auxiliary carriage, which is not shown. In this position the auxiliary instrument 9 with its tube 11 is guided so far through the end section 4 of the shank 1 that the jaw part 10 projects beyond the distal end of the shank 1. In this position, the jaw part 10 can be controlled via the lever 15, the suction and the rinsing channels are blocked by the tube 11.

Mounted on the distal side in front of the lever 15, there is a comparatively short release lever 24 which is likewise mounted in the lower side of the shank carrier 2. This lever 24 impinges the spring cam 22 in the downward direction via a cam 25 located within the shank carrier 2, such that on operation of the lever (pulling proximally), this able to be effected using a finger, the spring cam 22 (FIG. 4) moves downwardly and the spring pretensioned receiver 14 is released. By way of this, the receiver 14 is then moved into the rearward position shown in FIG. 3 in which the jaw part 10 of the auxiliary instrument 9 is inserted so far into the shank 1 that the end section is freely passable and may serve as a suction/rinsing channel.

The guiding tube 23 may be telescoped and at its proximal end comprises a pin with a circumferential groove, the pin engaging into a hole 51 of a laterally protruding part of the receiver 14 and here being automatically lockable. By operating a lever 26 (unlocking lever), this connection may be released. Then the whole receiver 14 together with the auxiliary instrument 9 may be withdrawn proximally from the carriage guide of the shank carrier 2, after which the auxiliary instrument 9 may be removed from the receiver 14 by loosening the knurled nut 19.

Figure 7:
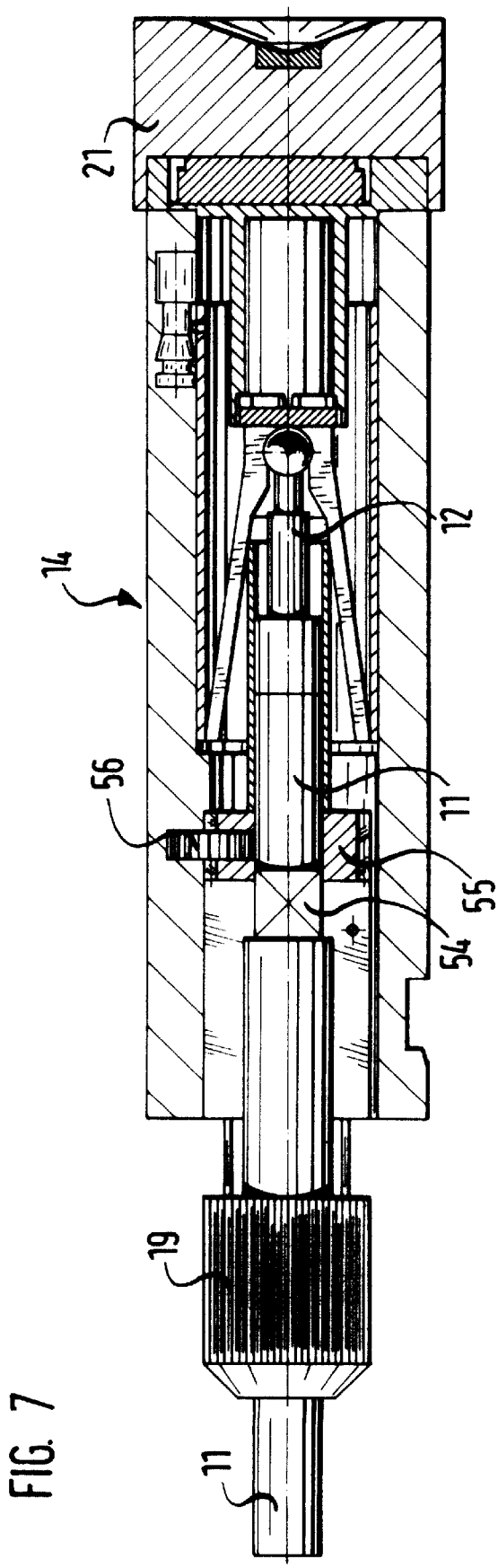

Since the instrument for the purpose of coagulation and cutting is subjected to HF current, the tube 11 as well as the shank 1 are covered with an insulating layer. The external components of the receiver, recognizable by way of FIG. 7, are likewise manufactured from an electrically insulating material. On the lower side of the hand grip 3 there is provided a connection 27 for the electrical high frequency supply. The guiding of the leads is effected from the connection 27 through the hand grip 3 into the shank carrier 2, where on the side distant to the receiver 14, of the upper leg (in FIG. 1 lying in the plane of the drawing) of the L-profile 17, there is arranged a housing 28 made of electrically insulating material. In this housing 28 there are arranged switching electronics which are not described in detail. On the outer side of the housing 28 there are provided two buttons 29 with which the current type (cutting current or coagulation current) may be selected and the current switched. Furthermore, the L-profile 17 comprises, as can be deduced from FIG. 1, and opening 30 through which a peg 31, rounded at its end sides, of a further switch or button arranged in the housing 28 projects, the switch or button being operated by the crossing receiver 14. In this way it is ensured that in the rearward position of the receiver (FIG. 3) when the auxiliary instrument is completely inserted into the shank 1, only the HF electrode 5 of the shank may be subjected to current and in the forward position of the receiver 14 (FIG. 1) only the auxiliary instrument 9 is subjectable to current.

There is provided a finger rest 32 next to the buttons 29. Likewise, laterally on the hand grip 3 (see FIG. 1) there is provided a thumb rest 33. Directly next to the thumb rest 33 two operating levers 34 and 35 are lead out through the retaining body 18 of the hand grip 3. As can be deduced by way of FIGS. 4 and 5, these levers 34, 35 are, via a lever mechanism, in connection with spring pretensioned squeezing bodies 36 which automatically squeeze off the hoses 7 led through the connecting cassette 8 when the levers 34 or 35 are not operated. On operation of a lever 34 or 35 a spring rod 37 running logitudinally within the hand grip 3 is pulled downwards, by which means the squeezing body lying on the hose 7 is moved away from the counter bearing 52 and opens the hose cross section. The force transmission is effected from the operating lever 35 onto a shaft 8 on whose other end again a lever 39 is mounted, this lever pulling the spring rod 37 with the squeezing body 36 fastened thereto downwards. The operating lever 35 operates in the same manner via a hollow shaft 40 and a lever 41.

Figure 6A:
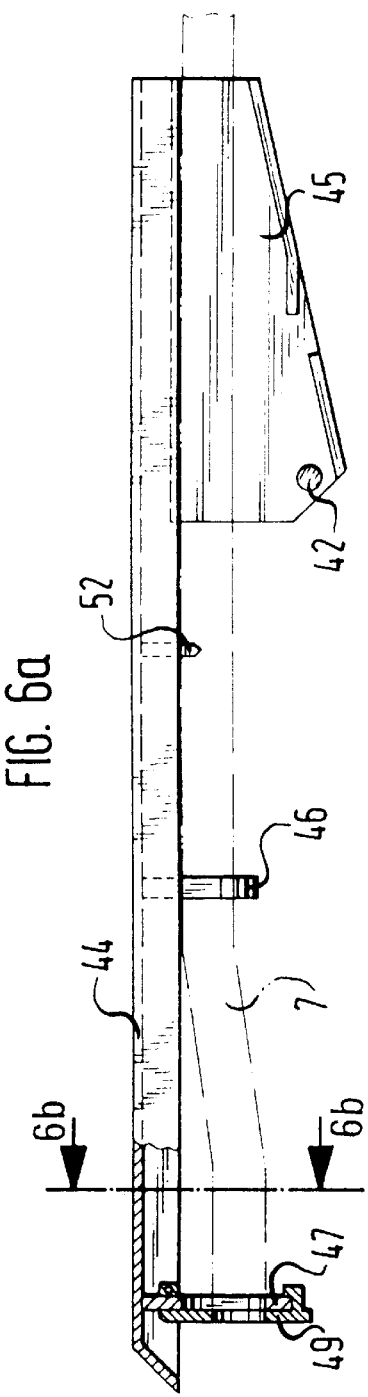
Figure 6C:
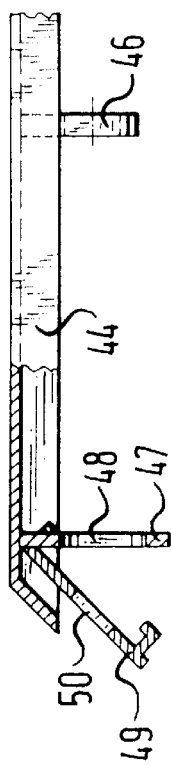
Figure 6B:
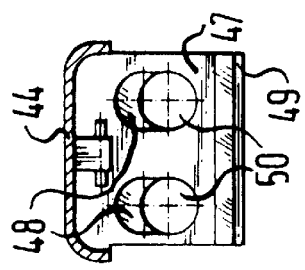

By way of FIGS. 6 the function of the connecting cassette 8 is shown. The connecting cassette with the hoses 7 located therein is roughly from below and proximally introduced into the grip part 3, that is into the open part of the U-profile 18, until the lateral guiding pins 42 engage into the recesses 43 of the retaining body 18 which are provided for them. In the end position shown in FIG. 1 the connecting cassette 8 automatically locks within the retaining body 18, an unlocking may be effected via an unlocking lever 53 on the lower side of the hand grip 3. The connecting cassette 8 consists of a roughly plate-shaped retaining body 44, which closes the U-profile and, as can be recognized from FIG. 1, protrudes downwards and proximally. In the protruding region the retaining body 44 is covered by a U-shaped guiding component 45. The hoses 7 are guided in the free space formed therebetween. A further guide in the form of clamping guide 46 open on one side is provided over half the length of the retaining body. The hoses 7 are pressed into this guide 46. Near to the connection location the retaining body 44 comprises, arranged perpendicular to it, a plate 47 in which there are provided two oval recesses 48 arranged next to one another, the smallest diameter corresponding roughly to the hose diameter. Assigned to this plate 47 there is a further plate 49 which is pivotably fastened to the plate 47 (or to the retaining body 44) and which at the free end engages over the plate 47 in a hook-like manner. The plate 49 likewise comprises oval recesses which, with their smallest axis, correspond roughly to the hose diameter. The recesses 48 and 50 are only partly aligned. On pivoting the plate 49 from the position shown in FIG. 6c into the position shown in FIG. 6a, the hose ends of the hoses 7 are clampingly fastened between the recesses 48 and 50 because these are so arranged displaced to one another in the direction of height, that the passage remaining in FIG. 6a is smaller than the cross section of the hose. The clamp-fastening in this region is particularly important since exactly directly behind this, the connection of the hoses to the free tube ends 6 is effected and therefore a defined position of the hoses must be ensured. On the plate 49 there is mounted a marking which is not shown and by way of which it is determined how far the free tube end must project beyond the plate 47 such that the desired position of the hoses within the connecting cassette 8, and thus a secure connection to the tube ends is guaranteed. The plate 49 is pivotingly fastened to the plate 47 with some play such that on account of the inherent tension of the hose, the position, locking with a positive fit, of the plate 49, is secured parallel to the plate 47. When the hoses are to be replaced on account of material fatigue or other reasons, then this may be effected in a simple manner after removing the connecting cassette 8 from the hand grip 3, in that the plate 49 is folded out from the plate 47, the hoses are removed and replaced by new ones. These are then to be pushed through the recesses 48 and 50 upto the marking, after which the plate 49 is folded up and the connecting cassette 8 may be inserted. Moreover, the oval shape of the recess 50 ensures that the plate 49 may be pivoted upwards without the hose ends hooking onto this plate.

Figure 8:
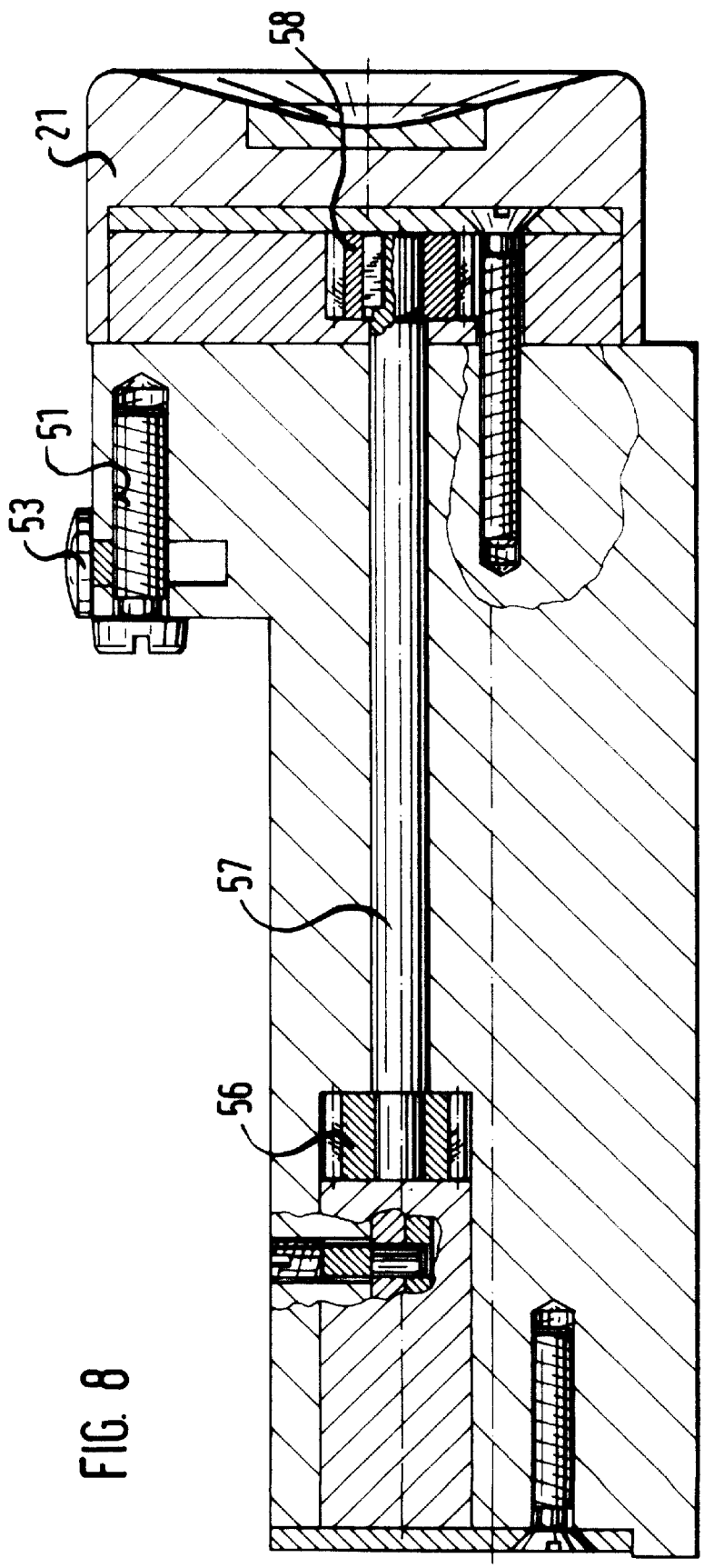

By way of FIGS. 7 and 8 the construction of the receiver 14 can be recognized in detail. The tube 11 of the auxiliary instrument is rigidly, but rotatably fastened in the axial direction by way of the knurled nut 19. For this purpose there is provided an annular projection on the tube 11. Within the receiver 14, the tube 11 comprises a section which is formed quadratically in cross section and which engages into a spur wheel 55 with a positive fit, this spur wheel camming with a smaller spur wheel 56 arranged displaced to it. As can be recognized in the longitudinal cross section according to FIG. 8, shown in a different plane, the spur wheel 56 is connected via a shaft 57 to a spur wheel 58 provided within the receiver 14 on the proximal side, which in turn is connected with a positive fit to the knurled wheel 21, so that by turning the knurled wheel 21, the tube 11 and thus the auxiliary instrument 9 is rotated about the shank axis.

As can be seen from FIG. 7, the receiver 14 is formed such that after tightening the knurled nut 19, the instrument 9 is rotatably, but undisplaceably fixed in the axial direction within the receiver 14. The tube 11 as well as the rod 12 are fastened within the receiver with a positive fit, this positive fit may only be released after undoing the knurled screw 19. Similar releasable fastenings are for example known from DE-A-94 09 979.

We claim:

1. A suction and rinsing instrument comprising:

a shank connected to a shank carrier;

a suction channel and a rinsing channel within said shank for supplying rinsing fluid into a body cavity and for removing fluid from the body cavity;

an auxiliary instrument including forceps, scissors which is interchangeably located within said suction channel;

a grip part connected to said shank carrier, said grip part having means for operating said auxiliary instrument as well as for controlling the supplying and removing of fluid, said grip part also includes a connecting cassette which is releasably arranged in said grip part;

a receiver connected to said shank carrier and traversable in an axial direction of the shank, said auxiliary instrument being fixed within said suction and rinsing instrument by said receiver;

operating means arranged near the grip part for traversing said receiver in the axial direction of said shank; and a tube connected to each of said suction and rinsing channels on the shank carrier, each tube having a first end and a second end, said first ends of said tubes face in a direction of said grip part, said tubes being connected via a connecting cassette to hoses which are exchangeably fixed within said connecting cassette.

2. An instrument according to claim 1, wherein the auxiliary instrument is rotatably arranged within the receiver, and wherein operating means for the preferable stepwise latchable turning of the auxiliary instrument within the receiver are provided near the grip part.

3. An instrument according to claim 1, wherein the shank connects to a roughly same-axis shank carrier on which the receiver is guided in a carriage manner and on which the grip part in the form of a hand grip is laterally arranged.

4. An instrument according to claim 1, wherein the shank is releasably fixed on the shank carrier.

5. A suction and rinsing instrument comprising:

a shank connected to an approximately same-axis shank carrier;

a suction channel and a rinsing channel connected to said shank for supplying and removing fluid from a body cavity;

an auxiliary instrument such as forceps or scissors, which is interchangeably located within said suction channel;

a grip part connected to said carrier shank, said grip part having means for operating said auxiliary instrument, as well as for controlling the supplying and removing of fluid;

a receiver connected to and slidably guided by said shank carrier and traversable in an axial direction of the shank, said auxiliary instrument being fixed within said receiver;

said grip part is in the form of a hand grip and being connected to said shank carrier in a lateral arrangement; and operating means, arranged near to the grip part, provided for traversing said receiver in the axial direction of said shank.

6. An instrument according to claim 5, wherein the shank comprises a distal end section of a smaller lumen and is formed at its distal end as a coagulation and/or cutting electrode.

7. An instrument according to claim 6, wherein the instrument automatically switches a current between the distal end section of the shank and the auxiliary instrument based on the position of the receiver on the shank carrier, such that when the auxiliary instrument is retracted or in a rearward position, the shank end is connected to a current source and when the auxiliary instrument is extended or in a forward position, the auxiliary instrument is adapted to be connected to the current source.

8. An instrument according to claim 5, wherein the auxiliary instrument is dimensioned such that in the forward end position of the receiver, it is guided within the distal end section on the shank carrier, its tool part however projecting beyond this section, and wherein in the retracted rearward end position, the tool part is inserted so far into the shank that fluid may flow through the distal end section.

9. An instrument according to claim 5, wherein the grip part on one side comprises a thumb rest as well as neighbouring levers for controlling the supply and removal of fluid, and wherein mounted in front of the grip part there is a finger ring arranged on a lever end, the finger ring serving the control of the auxiliary instrument and being pivotably mounted in the shank carrier.

10. An instrument according to claim 5, wherein the shank carrier comprises a retaining body having an L-shaped cross section with a lower leg and another leg, the receiver being guided in the shank carrier in a slidable manner, the lower leg being connected to a U-shaped retainer body of the grip part, and the other leg being connected to a housing part which includes electrical and/or electronic components for control of current.

11. An instrument according to claim 10, wherein a control means for a current type is on the housing part.

12. An instrument according to claim 10, wherein the receiver, on traversing to a forward position, tensions a spring arranged between the receiver and the shank carrier, and a release lever located on the housing releases the tension of the spring when depressed, automatically conveying the receiver from the forward position to a rearward position.

13. An instrument according to claim 5, wherein the shank is releasably fixed on the shank carrier.

* * * * *